United States Patent [19]

Giordano et al.

[11] Patent Number: 4,486,352

[45] Date of Patent: Dec. 4, 1984

[54] PROCESS FOR PREPARING 3ALPHA, 7BETA-DIHYDROXY-5BETA-CHOLANIC ACID

[75] Inventors: Claudio Giordano, Vicenza; Francesco Minisci, Milan; Mariano Meneghin, Revine-Lago; Giulio Perdoncin, Vicenza, all of Italy

[73] Assignee: Zambon S.p.A., Cappuccini, Italy

[21] Appl. No.: 481,299

[22] Filed: Apr. 1, 1983

[30] Foreign Application Priority Data

Apr. 2, 1982 [IT] Italy ............................... 20559 A/82

[51] Int. Cl.$^3$ ............................................. C07J 71/00
[52] U.S. Cl. .................................................. 260/397.1
[58] Field of Search ...................................... 260/397.1

[56] References Cited

U.S. PATENT DOCUMENTS

| | | | |
|---|---|---|---|
| 4,282,161 | 8/1981 | Guillemette et al. | 260/397.1 |
| 4,337,206 | 6/1982 | Gargani et al. | 260/397.1 |
| 4,379,093 | 4/1983 | Bonaldi et al. | 260/397.1 |

*Primary Examiner*—Elbert L. Roberts
*Attorney, Agent, or Firm*—Stevens, Davis, Miller & Mosher

[57] ABSTRACT

Process to reduce stereoselectively 3alpha-hydroxy-7-keto-5beta-cholanic acid to 3alpha,7beta-dihydroxy-5beta-cholanic acid in ter.alcohols by using, as reducing agent, sodium metal in the presence of other metal salts.

Examples of metal salts particularly useful are: potassium, cesium and rhubidium organic salts and, more particularly, potassium acetate or potassium ter.butylate.

2 Claims, No Drawings

PROCESS FOR PREPARING 3ALPHA, 7BETA-DIHYDROXY-5BETA-CHOLANIC ACID

This invention relates to a process for the stereoselective reduction of 3alpha-hydroxy-7-keto-5beta-cholanic acid to 3alpha,7-beta-dihydroxy-5beta-cholanic acid (ursodeoxycholic acid; UDCA) in ter.alcohols by using, as reducing agent, sodium metal in the presence of other metal salts.

The reduction of the 3alpha-hydroxy-7-keto-5beta-cholanic acid by means of sodium metal in alcohols is well-known since long time (Japanese patent application 52/78862). This process affords the formation of the mixture of UDCA and its epimeric form: 3alpha,7alpha-dihydroxy-5beta-cholanic acid (chenodeoxycholic acid, CDCA) in the ratio of 80/20.

A higher stereoselectivity has been obtained (Japanese patent application 52/7950) by reducing 3alpha-hydroxy-7-keto-5beta-cholanic acid with potassium metal in ter.butanol; in this way a mixture of 96/4 of UDCA/CDCA would be obtained. THe main disadvantages of this process are the high cost and the higher danger of potassium metal in comparison with sodium metal.

Now it has been surprisingly found that a stereoselectivity of 95–96% is obtained also when the reduction of 3alpha-hydroxy-7-keto-5beta-cholanic acid with sodium metal is carried out in the presence of a metal salt in ter.alcohol.

Examples of metal salt particularly useful are the organic salt of potassium, cesium and rhubidium and, more particularly, potassium acetate or potassium ter.-butylate.

Examples of tertiary alcohols particularly useful are ter.butyl-alcohol and ter.amyl-alcohol.

The molar ratio of sodium with respect to the used salts may range between 0.1 and 10.

Preferably the reduction is carried out by dissolving the ketone in alcohol in the presence of the metal salt and subsequent addition of sodium.

The reduction is carried out at temperature comprised between the room temperature and the boiling temperature of the solvent. When the reduction is complete UDCA is isolated by means of the usual techniques.

Sodium metal may be destroyed, for example, by adding methanol and water; after having removed the organic solvent, UDCA may be recovered by acidification and extraction with suitable solvents.

The following example are giving to illustrate the present invention, but in any case there are not limitative.

EXAMPLE 1

To a solution of potassium ter.butoxide (3.77 g, 33.6 mmols) and of 3alpha-hydroxy-7-keto-5beta-cholanic acid (2.5 g, 6.37 mmols) in ter.amyl-alcohol (50 ml), kept at the reflux, under nitrogen and under stirring, sodium is added (2.5 g, 0.109 gram-atoms). The reaction mixture is then kept under stirring at the reflux for 40'.

To the thus obtained solution methanol and then water are added until the destruction of the metal is complete.

The mixture is cooled and poured into water; the organic solvent is removed under vacuum. The aqueous phase is acidified with hydrochloric acid 1:1 up to pH 1 and extracted with ethylacetate (2×75 ml) at 40° C. By evaporation of the solvent under vacuum 2,4 gr of a solid product are obtained consisting of CDCA (6%) and UDCA (94%). The thus obtained product is esterified with methanol and subsequently crystallized from a mixture methanol/water to afford after hydrolyzation UDCA having a purity of 99.8%.

EXAMPLE 2

To a solution of potassium ter.butylate (3.77 g, 33.6 mmols) and 3alpha-hydroxy-7-keto-5beta-cholanic acid (2.5 g, 6.36 mmols) in ter.butyl-alcohol (50 ml), kept at the reflux under nitrogen and under stirring, sodium metal (1.75 g, 0.76 gram-atoms) is added. The reaction mixture is maintained under stirring and reflux for 2 hours and then worked up as disclosed in example 1; 2.5 g of the residue consisting of the CDCA (7%) and the UDCA (93) are thus obtained.

EXAMPLE 3

To a suspension of potassium acetate (59 g, 0.60 mol) in ter.amyl-alcohol (1000 ml), maintained at the reflux under nitrogen and under stirring, 3alpha-hydroxy-7-keto-5beta-cholanic acid (50 g, 0.127 mol) is added. To the thus obtained reaction mixture aliquots of sodium metal are added (40 g, 1.74 gram-atoms) in 5 hours. The reaction mixture is then worked up as in disclosed in example 1; 50 g of a mixture consisting of CDCA (5%), UDCA (94%) and unreacted acid (1) are thus obtained.

EXAMPLE 4

To a solution of 3alpha-hydroxy-7-keto-5beta-cholanic acid (0.25 g; 0.63 mmols) and ter.cesium-amylate (3.18 mmols) in ter.amylalcohol (3 ml), maintained at the reflux under nitrogen, small aliquots of sodium metal (0.25 g; 0.0108 gram-atoms) are added under stirring.

By following the procedure disclosed in example A, 0.24 g are obtained of a product consisting of UDCA (95%) and CDCA (5%).

EXAMPLE 5

To a solution of ter.rhubidium-amylate (11.7 mmols) and 3alpha-hydroxy-7-keto-5beta-cholanic acid (0.92 g; 2.34 mmols) in ter.amyl-alcohol (20 ml), maintained at the reflux under nitrogen, small aliquots of sodium metal (1 g; 0.0434 gram-atoms) are added under stirring.

By following the procedure disclosed in example A, 0.9 g are obtained of a product consisting of UDCA (95%) and CDCA (5%).

EXAMPLE 6

To a solution of 3alpha-hydroxy-7-keto-5beta-cholanic acid (0.5 g; 1.27 mmols) in ter.amyl-alcohol (10 ml), maintained at the reflux under nitrogen, rhubidium is added slowly (1.085 g; 0.0127 gram-atoms).

By following the procedure disclosed in example A, 0.49 g are obtained of a product consisting of UDCA (96%) and CDCA (4).

When this reduction is carryied out by using sodium or, respectively, potassium metal alone, the following results are obtained:

EXAMPLE A

To a solution of 3alpha-hydroxy-7-keto-5beta-cholanic acid (5 g, 12.7 mmols) in ter.amyl-alcohol (100 ml), maintained at the reflux under nitrogen and under stirring, small aliquots of potassium metal (5 g, 0.128 gram-atoms) are added in 5 minutes. The solution is then refluxed under stirring for 2 hours.

To the thus obtained solution methanol and water are added until the destruction of the metal is complete.

The mixture is cooled and poured into water; the organic solvent is removed under vacuum. The aqueous solution is acidified with hydrochloric acid 1:1 up to pH 1 and extracted with ethylacetate (2×75 ml) at 40° C. By evaporation of the solvent under vacuum a residue is obtained (4.97 g; 12.6 mmols; yield 99%) consisting of CDCA (5%) and UDCA (95%).

EXAMPLE B

By following the procedure disclosed in example A, but using sodium metal (5 g; 0.217 gram-atoms) instead of potassium metal and by carrying out the reaction for 4 hours, 5 g are obtained of a product consisting of CDCA (20%) and UDCA (80%).

What is claimed is:

1. Process for preparing 3 alpha, 7 beta-dihydroxy-5-beta-cholanic acid by the stereoselective reduction of 3-alpha-hydroxy-7-keto-5-beta-cholanic acid with sodium metal in ter.alkanols wherein for each mol of sodium metal are added from 0.1 to 10 mols of an organic salt of a metal selected from the group consisting of potassium, cesium and rubidium.

2. Process according to claim 1, characterized in that the metal salt is potassium acetate or potassium ter.butylate.

* * * * *